(12) United States Patent
Hite

(10) Patent No.: US 11,911,243 B2
(45) Date of Patent: *Feb. 27, 2024

(54) CERVICAL PAD

(71) Applicant: Outasite, LLC, Morrisville, NC (US)

(72) Inventor: Gwynne Marie Hite, Morrisville, NC (US)

(73) Assignee: OutaSite, LLC, Cary, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/752,255

(22) Filed: May 24, 2022

(65) Prior Publication Data
US 2022/0280346 A1    Sep. 8, 2022

Related U.S. Application Data

(63) Continuation of application No. 16/299,791, filed on Mar. 12, 2019, now Pat. No. 11,389,338, which is a continuation of application No. 14/860,073, filed on Sep. 21, 2015, now Pat. No. 10,226,387.

(60) Provisional application No. 62/052,824, filed on Sep. 19, 2014.

(51) Int. Cl.
*A61F 13/15* (2006.01)
*A61F 13/20* (2006.01)
*A61F 13/472* (2006.01)

(52) U.S. Cl.
CPC .... *A61F 13/2045* (2013.01); *A61F 13/47209* (2013.01); *A61F 2013/47281* (2013.01)

(58) Field of Classification Search
CPC ............ A61F 13/2045; A61F 13/47209; A61F 2013/47281
See application file for complete search history.

(56) References Cited

U.S. PATENT DOCUMENTS

| 2,309,868 A | 2/1943 | Robertson |
| 3,128,767 A | 4/1964 | Nolan |
| 3,216,422 A * | 11/1965 | Steiger ...................... A61F 6/08 604/330 |

(Continued)

FOREIGN PATENT DOCUMENTS

| CA | 2137769 A1 | 5/1996 |
| EP | 0134671 A1 | 4/1987 |

(Continued)

OTHER PUBLICATIONS

Author Unknown, "Reusable Resolutions & Resuable Instead Softcup," The Vagina Monologues, Dec. 26, 2011, vagmonologues.blogspot.com/2011/12/reusable-resolutions-reusable-instead.html, 13 pages.

(Continued)

*Primary Examiner* — Jacqueline F Stephens

(74) *Attorney, Agent, or Firm* — WITHROW & TERRANOVA, PLLC

(57) ABSTRACT

A cervical pad is provided for absorbing and collecting body fluids. The cervical pad comprises a resilient circular rim configured to span a vaginal opening adjacent the cervical os. A central body portion spans the area defined by the rim. The body portion includes a pad comprising an upper membrane layer, a lower membrane layer sealingly connected to the rim, and a flexible absorbent insert is disposed in a space defines between the inner membrane layer and the outer membrane layer.

23 Claims, 3 Drawing Sheets

(56) References Cited

U.S. PATENT DOCUMENTS

| | | |
|---|---|---|
| 3,658,057 A | 4/1972 | Climber |
| 3,983,874 A | 10/1976 | Davis et al. |
| 4,198,976 A | 4/1980 | Drobish et al. |
| 4,200,090 A | 4/1980 | Drobish |
| 4,219,016 A | 8/1980 | Drobish et al. |
| 4,304,226 A | 12/1981 | Drobish et al. |
| 4,320,751 A | 3/1982 | Loeb |
| 4,322,463 A | 3/1982 | Goepp et al. |
| 4,326,510 A | 4/1982 | Buckles |
| 4,363,318 A | 12/1982 | Goepp et al. |
| 4,369,219 A | 1/1983 | Goepp et al. |
| 4,369,773 A | 1/1983 | Chvapil |
| 4,381,771 A | 5/1983 | Gabbay |
| 4,384,572 A | 5/1983 | Goepp |
| 4,393,871 A | 7/1983 | Vorhauer et al. |
| 4,401,534 A | 8/1983 | Goepp et al. |
| 4,450,836 A | 5/1984 | Goepp et al. |
| 4,467,789 A | 8/1984 | Goepp et al. |
| 4,517,970 A | 5/1985 | Goepp et al. |
| 4,543,949 A | 10/1985 | Goepp et al. |
| 4,589,880 A | 5/1986 | Dunn et al. |
| 4,703,752 A | 11/1987 | Gabbay |
| 4,848,363 A | 7/1989 | Cattanach |
| 4,858,624 A | 8/1989 | Shihata |
| 4,959,216 A | 9/1990 | Daunter |
| 4,989,618 A | 2/1991 | Shihata |
| 5,000,749 A | 3/1991 | LeVeen et al. |
| 5,070,889 A | 12/1991 | Leveen et al. |
| 5,156,164 A | 10/1992 | LeVeen et al. |
| 5,207,232 A | 5/1993 | Shihata |
| 5,231,992 A | 8/1993 | Leon |
| 5,295,984 A | 3/1994 | Contente et al. |
| 5,527,534 A | 6/1996 | Myhling |
| 5,592,949 A | 1/1997 | Moench et al. |
| 5,617,877 A | 4/1997 | Moench et al. |
| 5,771,900 A | 6/1998 | Austin et al. |
| 5,928,184 A | 7/1999 | Etheredge et al. |
| 6,126,616 A | 10/2000 | Sanyal |
| 6,177,606 B1 | 1/2001 | Etheredge et al. |
| 6,264,638 B1 | 7/2001 | Contente |
| 6,332,878 B1 | 12/2001 | Wray et al. |
| 6,796,973 B1 | 9/2004 | Contente et al. |
| 7,192,630 B2 | 3/2007 | Ziltener et al. |
| 10,226,387 B2 * | 3/2019 | Hite ................ A61F 13/47209 |
| 10,383,775 B2 | 8/2019 | Edmunds |
| 11,389,338 B2 * | 7/2022 | Hite ................ A61F 13/47209 |
| 2007/0289598 A1 | 12/2007 | LaBarre et al. |
| 2008/0200888 A1 | 8/2008 | Gooch et al. |
| 2016/0081860 A1 | 3/2016 | Hite |
| 2016/0278988 A1 | 9/2016 | Knox |
| 2019/0201248 A1 | 7/2019 | Hite |

FOREIGN PATENT DOCUMENTS

| | | |
|---|---|---|
| NO | 0115757 A1 | 8/2001 |
| WO | 8701581 A1 | 3/1987 |
| WO | 9108779 A1 | 6/1991 |
| WO | 9400168 A1 | 1/1994 |
| WO | 9843687 A1 | 10/1998 |

OTHER PUBLICATIONS

Beppy, "Beppy Soft + Comfort TamponsDRY envelope (4pcs)," accessed Oct. 4, 2021 from https://www.beppy.com/en/product/beppy-soft-comfort-tampons-dry-envelope-4pcs/, 2 pages.

Beppy, "Beppy Soft + Comfort TamponsWET envelope (4pcs)," accessed Oct. 4, 2021 from https://www.beppy.com/en/product/beppy-soft-comfort-tampons-wet-envelope-4pcs/, 2 pages.

Beppy, "Feel Free, Do What You Like, Every Day of the Month!" available as early as Dec. 2019 from https://www.beppy.com/en/home/, 4 pages.

Cattanach, J., "The Gynaeseal diaphragm tampon," The Medical Journal of Australia, vol. 152, Issue 1, Jan. 1990, 2 pages.

Diva International Inc., "Goodbye Tampons," available as early as Dec. 2019 from https://divacup.com/, 7 pages.

The Flex Company, "Shop Flex Disc | Flex® Sustainable Period Products," available as early as Dec. 2019 from https://flexfits.com/, 6 pages.

JOYDIVISION, "Discover stringless Soft-Tampons by JOYDIVISION," available as early as Dec. 2019 from https://joydivision.de/en/all-products/soft-tampons-professional-box-of-50, 4 pages.

North, B. et al., "Preclinical, Clinical, and Over-the-Counter Postmarketing Experience with a New Vaginal Cup: Menstrual Collection," Journal of Women's Health, vol. 20, No. 2, Feb. 13, 2011, 18 pages.

Sree, "Recent interventions in barrier contraceptive methods," Obs &Gyn, Nov. 22, 2013, srsree.blogspot.com/2013/11/recent-interventions-in-barrier.html, 6 pages.

Williams, L., "What is a Softcup?" Apr. 12, 2012, SheKnows, https://www.sheknows.com/health-and-wellness/articles/953517/what-is-a-softcup/, 11 pages.

Non-Final Office Action for U.S. Appl. No. 14/860,073, dated Dec. 29, 2017, 10 pages.

Applicant-Initiated Interview Summary for U.S. Appl. No. 14/860,073, dated Jul. 3, 2018, 3 pages.

Notice of Allowance for U.S. Appl. No. 14/860,073, dated Oct. 29, 2018, 8 pages.

Corrected Notice of Allowability for U.S. Appl. No. 14/860,073, dated Dec. 3, 2018, 4 pages.

Issue Notification for U.S. Appl. No. 14/860,073, dated Feb. 20, 2019, 1 page.

Non-Final Office Action for U.S. Appl. No. 16/299,791, dated Aug. 30, 2021, 11 pages.

Notice of Allowance for U.S. Appl. No. 16/299,791, dated Apr. 1, 2022, 8 pages.

* cited by examiner

CERVICAL PAD

CROSS-REFERENCES

This application is a continuation application of U.S. application Ser. No. 16/299,791, filed Mar. 12, 2019, entitled "CERVICAL PAD," which is a continuation application of U.S. application Ser. No. 14/860,073, filed Sep. 21, 2015, entitled "CERVICAL PAD," issued as U.S. Pat. No. 10,226,387, which claims the benefit of U.S. provisional application No. 62/052,824, filed Sep. 19, 2014. The contents of each application are incorporated herein by reference in their entirety, and the benefit of the filing dates of the applications is hereby claimed for all purposes that are legally served by such claim for the benefit of the filing dates.

BACKGROUND

A feminine hygiene device is described and, more particularly, an intravaginal device comprising a cervical pad for absorbing and collecting body fluids and other vaginal discharge.

Conventional articles for absorption of vaginal discharge and other bodily fluids, such as menstrual napkins, tampons, and non-absorbent collection reservoirs, often leak during active use. Further, there is no solution among conventional absorbent devices for a barrier for use during sexual intercourse or other sexual contact.

For the foregoing reasons, there is a need for an intravaginal device that can be conveniently and reliably used for absorbing and collecting vaginal discharge and other body fluids, particularly during menses. Ideally, the fluid will be retained by the device during movement of or pressure on the device during use.

SUMMARY

A cervical pad is provided to be disposed in a vaginal opening adjacent to a cervical os for absorbing and collecting body fluids. The cervical pad comprises a resilient circular rim configured to span the vaginal opening adjacent the cervical os. A central body portion spans the area defined by the rim. The body portion includes a pad comprising an upper membrane layer, a lower membrane layer sealingly connected to the rim, and a flexible absorbent insert is disposed in a space defined between the inner membrane layer and the outer membrane layer.

BRIEF DESCRIPTION OF THE DRAWINGS

For a more complete understanding of the present invention, reference should now be had to the embodiments shown in the accompanying drawings and described below. In the drawings.

DESCRIPTION

Figure 1:
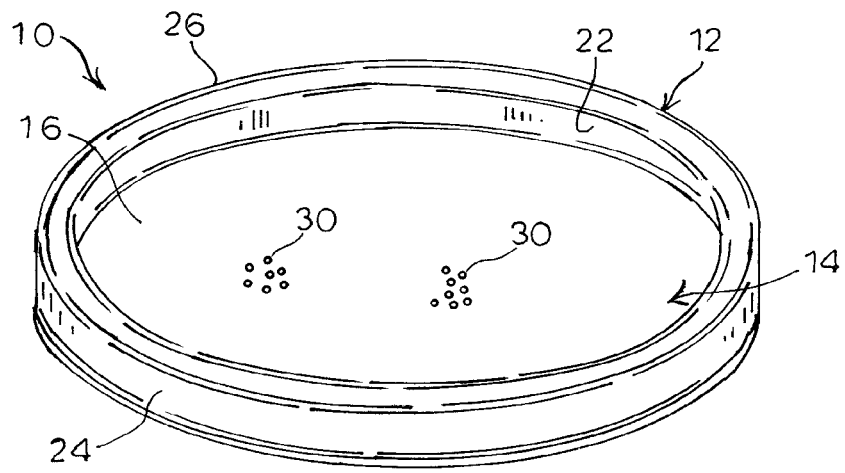
FIG. 1 is a perspective view of an embodiment of a cervical pad.
Figure 4:
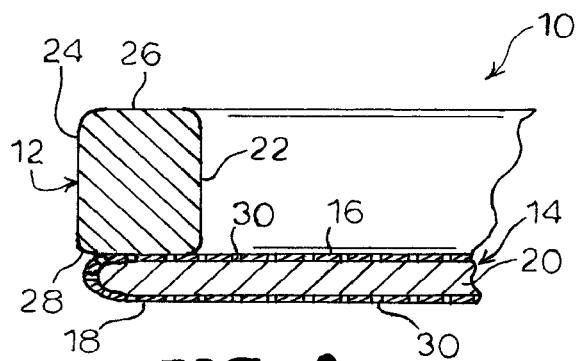
FIG. 4 is an up-close view of a portion of the cervical pad as shown in FIG. 3.
Figure 5:
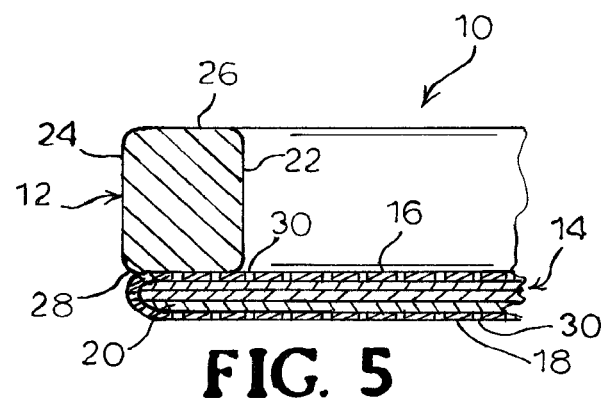
FIG. 5 is an up-close view of a portion of another embodiment of a cervical pad.
Figure 2:
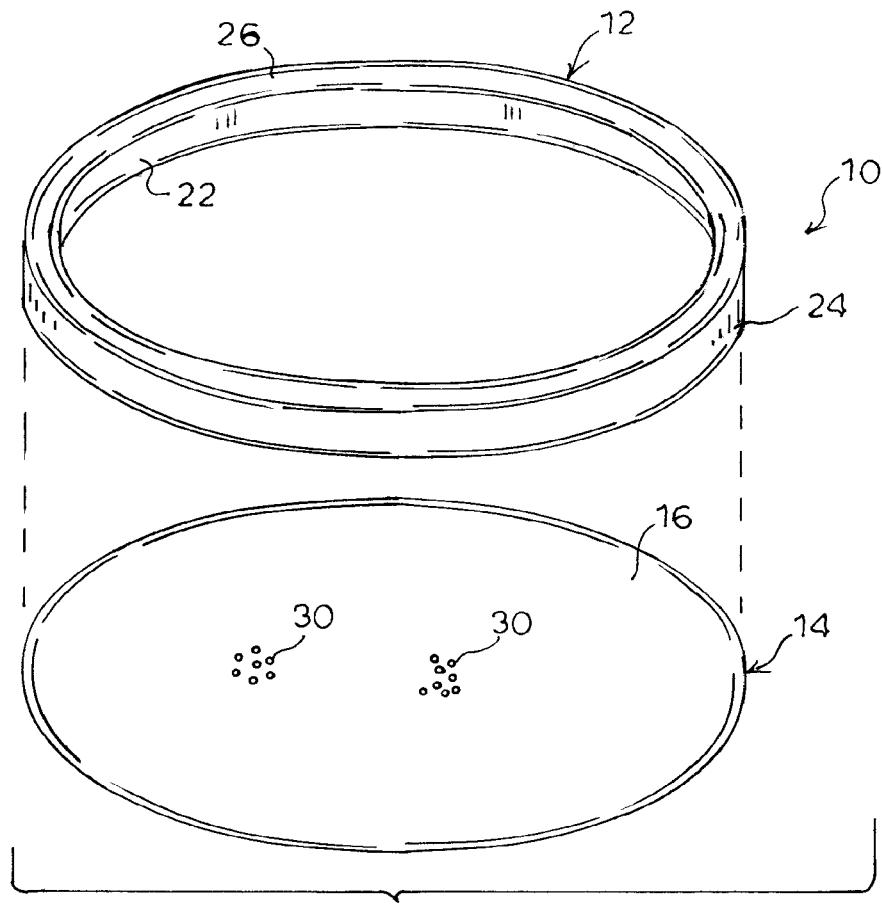
FIG. 2 is an exploded perspective view of the cervical pad as shown in FIG. 1.
Figure 3:
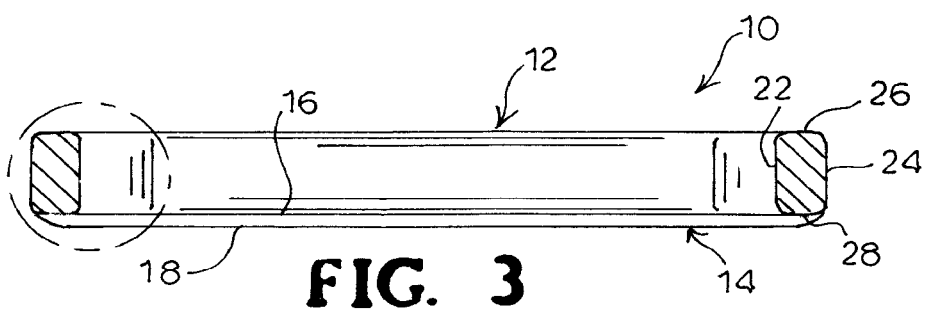
FIG. 3 is an elevated transverse cross-section view of the cervical pad as shown as shown in FIG. 1.

Referring now to FIGS. 1-3, wherein like reference numerals indicate the same or similar parts throughout the several views, a cervical pad is shown and generally designated at 10. The cervical pad 10 comprises a resilient elastomeric circular rim 12 spanned by a central body portion 14. The body portion 14 of the cervical pad 10 comprises a flexible absorbent reservoir. The absorbent reservoir is a layered pad, including an upper membrane layer 16 and a lower membrane layer 18 formed of thin, impervious, elastomeric film material sealingly connected to the rim 12. A flexible absorbent insert 20 is disposed in a space defined between the inner membrane layer 16 and the outer membrane layer 18. As will be described more fully below, the cervical pad 10 functions as a barrier device to cover the cervical os for absorbing and collecting body fluids and other vaginal discharge.

As shown in FIG. 3, the rim 12 has a generally rectangular cross-section with an inner side surface 22 substantially parallel to an outer side surface 24. The upper edge 26 and the lower edge 28 of the rim 12 are smoothly rounded making the cervical pad 10 easier to insert into position for use and minimizing the discomfort to a user when the cervical pad 10 is in the vaginal canal. In the embodiment shown, the height of the rim 12 is greater than the thickness of the rim.

The cervical pad 10 is configured to be positioned loosely around the cervix of a user. The rim 12 is dimensioned to generally form a gasket between the cervix and the wall of the vagina and prevent leakage past the cervical pad. In one embodiment, the rim 12 of the cervical pad 10 is formed entirely of a suitable elastomer which is stable, flexible and non-irritating. However, it is understood that alternative rim 12 constructions may be used. In one embodiment, the outer diameter of the rim 12 is about two inches to about four inches (about five centimeters to about ten centimeters) and the inner diameter of the rim 12 is about % inches to about 2 1 h inches (about 2 centimeters to about 6 centimeters). Accordingly, the rim 12 has a range of thicknesses. In one embodiment, the rim 12 has a thickness of about 1;4 inch (about six millimeters). It is understood that the diameter and the cross-sectional thickness of the rim 12 will depend upon the stiffness of the rim material used. The rim 12 should be flexible enough to be easily deformed and facilitate insertion into position in the vagina, and yet be sufficiently resilient enough to distend into contact with the vaginal wall and exert sufficient radial outward force to hold the cervical pad 10 in position and prevent vaginal discharge from leaking between the rim 12 and the vaginal wall.

It is understood that the rim 12 need not be circular and can have other shapes, for example, a "rowboat" shape. Other suitable shapes include, but are not limited to, square, rectangular, oval, trapezoidal, and other shapes defining a closed loop. Preferably, the cervical pad 10 has a shape which anchors the cervical pad in a desired position in the vaginal canal for blocking fluid flow past the cervical pad 10.

The upper and lower flexible membrane layers 16, 18 are formed of a substantially impervious material, such as a stable, nonirritating, flexible polymer which is non-absorbent to liquid. The membrane layers 16, 18 extend across the area defined by the rim 12 and are secured peripherally to the lower edge 28 of the rim 12 to form an essentially flat, impermeable central body portion 14 having a top surface and a bottom surface. The membrane layers 16, 18 can be attached to the circumferences of the rim by conventional sealing means, such as heat sealing, adhesives or any other conventional methods. The membrane layers 16, 18 are flexible enough to return to their original shape after being folded and compressed during insertion of the cervical pad 10. The thickness of the membrane layers 16, 18 is preferably greater that about one ten thousandths of an inch (about two micrometers). It is understood that the thickness of the membrane layers 16, 18 will depend upon the properties of the material used, which is suitable so that the body portion 14 will have sufficient strength and flexibility.

The membrane layers 16, 18 are fenestrated, defining pass through apertures 30 for allowing vaginal discharge to drain into the space between the membrane layers 16, 18. The total open area defined by the apertures 30 is preferably between about five percent and about ninety five percent of the area defined by the rim 12. In general, the number and size of the apertures 30 in the membrane layers 16, 18 are chosen such that the flow of menses or other vaginal discharge is enabled into the space at a desired flow rate when the cervical pad is in use while inhibiting the exit of fluid from the space between the membrane layers 16, 18. If the apertures 30 provided are too few or too small, the rate of absorbency in use may be reduced, while if the apertures are too large, too many, or improperly placed, the cervical pad 10 may leak in use. In one embodiment, the aperture diameter is about 0.2 inches to about 0.4 inches (about 5 to about 10 millimeters). The density of apertures per square inch is about 2 apertures per square inch to about 8 apertures per square inch. A fenestrated membrane material formed from, for example, polyethylene, is available from several medical products companies. A suitable membrane may be sourced from Southmedic Inc. of Canada.

The flexible absorbent insert 20 is disposed within the space between the membrane layers 16, 18 of the body portion 14 for absorbing fluid that enters the space. The absorbent insert 20 has a diameter at least up to the inside diameter of the rim 12, which allows the insert 20 to fit snugly within the inner circumference of the rim 12. It is understood that the absorbent insert 20 need not completely fill the space, as long as fluid is inhibited from exiting the space downstream of the cervical pad 10. The flexible material of the absorbent insert 20 allows the insert to fold when the cervical pad 10 is compressed for insertion into the vaginal canal and to spring back into place when the deforming pressure on the rim 12 is released.

The material of the absorbent insert 20 absorbs and retains the menstrual fluid within the cervical pad 10. Virtually any absorbent material may be used. Suitable material for the absorbent insert 20 may comprise, for example, natural fibers such as cotton, synthetic fibers such as rayon or fluff pulp, needle-punched engineered absorbents, fiber tows, tow webs, cellulosic sponge materials, and blends thereof. In addition, the absorbent material may be a superabsorbent material, including a material that forms a gel upon contact with moisture, for example, sodium carboxy methyl cellulose. The absorbent insert 20 may also be a woven or a non-woven flexible fabric. For example, it may be a non-woven fabric made of fibers held together by a suitable binder and formed with openings to afford the necessary porosity or perv10usness.

The volume of the space between the membrane layers 16, 17 and the amount and absorbency of the absorbent insert 20 will determine the total absorbency of the cervical pad 10. These parameters can be varied as desired to design a cervical pad 10 having a predetermined absorbency. In addition, the appropriate number and size of apertures 30 in the membrane layers 16, 18 can be determined based upon, among other parameters, the degree of absorbency of the absorbent material.

The rim 12 and the body portion 14 of the cervical pad 10 define a generally concave recess, which creates a cavity for collecting vaginal discharge. The amount of vaginal discharge that can be collected is a function of the depth of the cervical pad 10. In one embodiment, the depth of the cervical pad 10 measured from the top edge of the rim 12 to the outer surface of the outer membrane layer of the body portion 14 is preferably about 0.04 inches to about 0.4 inches (about 0.1 centimeters to about 1 centimeter). The thickness of the body portion 14 is within a range of about 0.004 inches to 0.2 inches (about 0.1 millimeters to about 5 millimeters). An increased depth may provide increased volume for discharge collection, which increases the amount of time that the cervical pad 10 can be worn. The conflicting goals of increased collection volume and increased comfort are satisfactorily balanced when the height of the rim 12 is no less than approximately about 0.2 inches (about 5 millimeters) and no more than about 0.4 inches (about 10 millimeters). The volume of the collection space is preferably about one to about two ounces (about 30 milliliters to about 60 milliliters).

The deformability of the cervical pad 10 makes possible a single cervical pad having a size which suits most women. Therefore, the cervical pad 10 can be economically manufactured in a single size and still be acceptable for most women. It may be advantageous to manufacture the cervical pad in three different sizes: (1) a junior size for teenage girls; (2) an intermediate size for nulliparous women (i.e., those who have not had a child); and (3) a large size for parous women.

In use, the cervical pad 10 is held in a hand and diametrically opposed portions of the rim 12 are pressed into contact with each other between two fingers, which may, for example, be the thumb and middle finger of the same hand. In this position, the rim 12 assumes a figure-eight-shaped configuration. The cervical pad is 10 inserted into the vaginal canal adjacent the cervix until a leading portion of the rim 12 and the inner membrane 16 are in position behind the cervix and behind the pubic bone. The compression applied by the fingers is then released, allowing the rim 12 to elastomerically restore itself to its initial, generally circular configuration.

Figure 6:
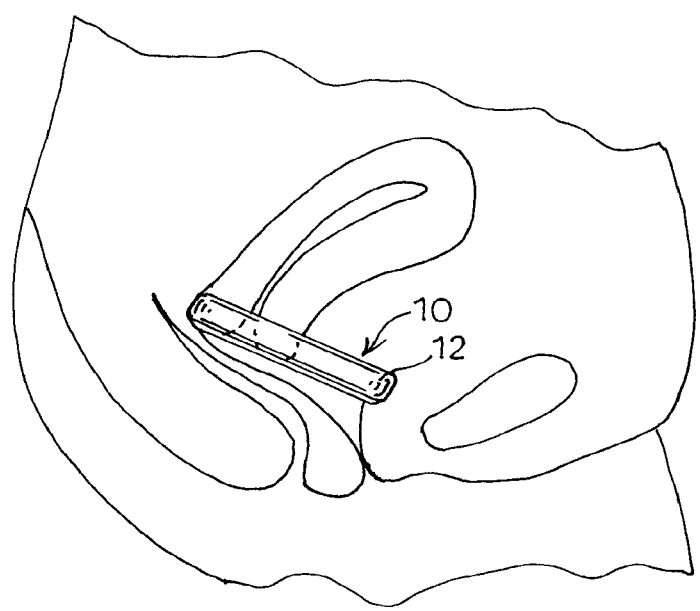
FIG. 6 is schematic view of the cervical pad as shown in FIG. 1 in a position in a vaginal canal.

When the cervical pad 10 is in position, the central body portion 14 is positioned below the cervix covering the cervical os (FIG. 6). In this position the rim 12 contacts and exerts a resilient, radially outwardly directed force for conforming against the wall of the vaginal canal. The cervical pad 10 is held in position by this resilient outward force and by compression of the vaginal wall on the rim 12. The outwardly radial force of the resilient rim 12 is sufficient to effectively prevent menses or other vaginal discharge from passing between the rim 12 and the wall of the vaginal canal.

The cervical pad 10 provides a reservoir within the cavity for receiving vaginal discharge exiting the cervix, including menstrual fluid, uterine, cervical and mucosal discharge, particularly blood and tissue sloughed off from a woman's uterus during menstruation. Vaginal discharge from the cervix is collected within the body portion 14 of the cervical pad 10. The amount of discharge typically generated during a menstrual cycle is two to eight tablespoons (thirty to one hundred twenty milliliters). However, the cervical pad 10 is not meant to be worn for a full cycle. In one embodiment, the dimensions of the cervical pad 10 are such that it can fit comfortably in the genital tract of the user for as long as 6 to 8 hours. During this 6 to 8 hour time period, a woman typically discharges about one teaspoon (five milliliters) of menstrual fluid, although much larger volumes of liquid may be discharged during heavy flow periods. Because of the design of the rim 12, the cervical pad 10 is easily retained in the vagina positioned over the cervical os without being readily displaced. While in place, the cervical pad 10 provides a barrier for vaginal discharge during activity, including intercourse or other sexual contact.

After a period of time, the cervical pad 10 is removed from the vaginal canal and disposed of along with the collected vaginal discharge. To remove the cervical pad 10, the user inserts a finger into the vaginal canal and grasps a radially inner surface of the rim 12. Since the body portion 14 is flexible, the finger can be easily pushed through the plane containing the bottom edge of the rim 12, allowing the user to grasp the rim 12. The cervical pad 10 may also be removed by placing the finger over the top edge of the rim 12 and using the finger and the thumb to grasp the rim 12 for removal.

The cervical pad 10 can be manufactured by any suitable method. For example, the rim 12 and membrane layers 16, 18 can be thermoformed, molded, or otherwise formed into a circular or other shape. The absorbent insert 20 can then be inserted between the membrane layers 16, 18 and the edges of the membrane layers 16, 18 sealed to the rim 12.

The cervical pad 10 has many advantages, including providing a vaginal discharge collection device that can be used to collect menstrual discharge during sexual intercourse. It does not obstruct the vaginal canal like a tampon, or tampon-like product, that includes a string jutting down out of vagina. It does not consist of bulk or external wear of a feminine hygiene pad or other pads. The cervical pad 10 does not leak as does a padless vaginal fluid collection reservoir. The cervical pad 10 allows collection of fluid into the body portion 14 through the apertures 30 but inhibits exit of the fluid. The ability of the cervical pad 10 to absorb and hold collected fluid provides a barrier against the blood environment. The cervical pad 10 resists leakage of fluid during use. The cervical pad 10 provides women with a novel barrier which is easy to use and does not require individual fitting.

I claim:

1. A cervical pad, comprising:
    a rim;
    a first membrane layer sealingly connected to the rim, the first membrane layer configured to allow passage of vaginal discharge;
    a second membrane layer sealingly connected to the rim, the second membrane layer configured to allow passage of vaginal discharge; and
    an absorbent insert at least partially disposed between the first membrane layer and the second membrane layer, the absorbent insert configured to absorb and collect vaginal discharge.

2. The cervical pad as recited in claim 1, wherein the rim has a generally rectangular transverse cross-section with an inner side surface substantially parallel to an outer side surface.

3. The cervical pad as recited in claim 2, wherein a height of the rim is greater than a thickness of the rim.

4. The cervical pad as recited in claim 1, wherein an outer diameter of the rim is about two inches to about four inches.

5. The cervical pad as recited in claim 1, wherein an inner diameter of the rim is about ¾ inches to about 2½ inches.

6. The cervical pad as recited in claim 1, wherein a thickness of the rim is about ¼ inch.

7. The cervical pad as recited in claim 1, wherein the first and second membrane layers comprise a substantially impervious material.

8. The cervical pad as recited in claim 1, wherein the first and second membrane layers are fenestrated.

9. The cervical pad as recited in claim 8, wherein a total open area defined by apertures is between about 5% and about 95% of an area defined by the rim.

10. The cervical pad as recited in claim 8, wherein a diameter of the apertures is about 0.2 inches to about 0.4 inches, and a density of apertures per square inch is about 2 apertures per square inch to about 8 apertures per square inch.

11. The cervical pad as recited in claim 1, wherein a material for the absorbent insert comprises at least one of natural fibers, synthetic fibers, needle-punched engineered absorbents, fiber tows, tow webs, or cellulosic sponge materials.

12. The cervical pad as recited in claim 1, wherein a material for the absorbent insert comprises a superabsorbent material.

13. The cervical pad as recited in claim 12, wherein a material for the absorbent insert includes sodium carboxy methyl cellulose.

14. The cervical pad as recited in claim 1, wherein a depth of the cervical pad is about 0.04 inches to about 0.4 inches.

15. The cervical pad as recited in claim 1, wherein a thickness of the rim is about 0.004 inches to 0.2 inches.

16. The cervical pad as recited in claim 1, wherein a volume of a collection space defined by the rim is about two ounces.

17. The cervical pad as recited in claim 1, wherein the first membrane layer, the second membrane layer, and the absorbent insert are generally flat.

18. The cervical pad as recited in claim 1, wherein the first membrane layer and the second membrane layer are generally flat.

19. The cervical pad as recited in claim 1, wherein the cervical pad comprises a non-woven fabric.

20. The cervical pad as recited in claim 1, wherein an outer diameter of the cervical pad is greater than an inner diameter of the rim.

21. The cervical pad as recited in claim 1, wherein the cervical pad is positioned below a lower edge of the rim.

22. The cervical pad as recited in claim 1, wherein the first membrane layer and the second membrane layer comprise polyethylene.

23. The cervical pad as recited in claim 1, wherein the first membrane layer and the second membrane layer are fenestrated.

* * * * *